United States Patent
Okamoto et al.

(10) Patent No.: US 9,221,732 B2
(45) Date of Patent: Dec. 29, 2015

(54) METHOD FOR SEPARATING 1-CHLORO-3,3,3-TRIFLUOROPROPENE AND HYDROGEN FLUORIDE, AND METHOD FOR PRODUCING 1-CHLORO-3,3,3-TRIFLUOROPROPENE BY USING SAME

(71) Applicant: Central Glass Company, Limited, Ube-shi, Yamaguchi (JP)

(72) Inventors: Satoru Okamoto, Kawagoe (JP); Satoshi Yoshikawa, Saitama (JP); Fuyuhiko Sakyu, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/413,907

(22) PCT Filed: Jul. 5, 2013

(86) PCT No.: PCT/JP2013/068500
§ 371 (c)(1),
(2) Date: Jan. 9, 2015

(87) PCT Pub. No.: WO2014/010530
PCT Pub. Date: Jan. 16, 2014

(65) Prior Publication Data
US 2015/0203424 A1    Jul. 23, 2015

(30) Foreign Application Priority Data

Jul. 11, 2012 (JP) .................................. 2012-155526
Aug. 7, 2012 (JP) .................................. 2012-175435
Jul. 3, 2013 (JP) .................................. 2013-140082

(51) Int. Cl.
*C07C 17/38* (2006.01)
*C07C 17/23* (2006.01)

(52) U.S. Cl.
CPC ................. *C07C 17/38* (2013.01); *C07C 17/23* (2013.01)

(58) Field of Classification Search
None
See application file for complete search history.

(56) References Cited

U.S. PATENT DOCUMENTS

| | | | |
|---|---|---|---|
| 6,013,846 | A | 1/2000 | Wismer et al. |
| 6,018,084 | A | 1/2000 | Nakada et al. |
| 6,844,475 | B1 | 1/2005 | Tung et al. |
| 7,803,975 | B2 | 9/2010 | Knapp |
| 8,426,656 | B2 | 4/2013 | Merkel et al. |
| 2005/0033097 | A1 | 2/2005 | Tung et al. |
| 2008/0011678 | A1 | 1/2008 | Knapp |
| 2010/0308259 | A1 | 12/2010 | Knapp |
| 2011/0172472 | A1 | 7/2011 | Sakyu et al. |
| 2011/0201853 | A1 | 8/2011 | Tung et al. |
| 2011/0218370 | A1* | 9/2011 | Elsheikh et al. ............ 570/236 |
| 2011/0245549 | A1 | 10/2011 | Merkel et al. |

FOREIGN PATENT DOCUMENTS

| | | |
|---|---|---|
| JP | 9-183740 A | 7/1997 |
| JP | 11-180908 A | 7/1999 |
| JP | 11-279088 A | 10/1999 |
| JP | 2007-501843 A | 2/2007 |
| JP | 2009-543787 A | 12/2009 |
| JP | 2012-158552 A | 8/2012 |
| WO | WO 2010/035748 A1 | 4/2010 |
| WO | WO 2011/103035 A2 | 8/2011 |
| WO | WO 2011/126692 A2 | 10/2011 |

OTHER PUBLICATIONS

International Search Report (PCT/ISA/210) dated Oct. 1, 2013 with English translation (five pages).
Japanese-language Written Opinion (PCT/ISA/237) dated Oct. 1, 2013 (four pages).

* cited by examiner

*Primary Examiner* — Brian J Davis
(74) *Attorney, Agent, or Firm* — Crowell & Moring LLP

(57) ABSTRACT

A separation method of 1-chloro-3,3,3-tetraluofopropene and hydrogen fluoride according to the present invention includes reducing the hydrogen chloride content of a mixture containing hydrogen chloride, 1-chloro-3,3,3-tetrafluoropropene and hydrogen fluoride, thereby causing phase separation of the mixture so as to obtain an upper phase predominantly containing the hydrogen fluoride and a lower phase predominantly containing the 1-chloro-3,3,3-tetrafluoropropene. This separation method is industrially economically advantageous since the 1-chloro-3,3,3-tetraluofopropene and the hydrogen fluoride can be separated rapidly by simple operation.

4 Claims, No Drawings

US 9,221,732 B2

METHOD FOR SEPARATING 1-CHLORO-3,3,3-TRIFLUOROPROPENE AND HYDROGEN FLUORIDE, AND METHOD FOR PRODUCING 1-CHLORO-3,3,3-TRIFLUOROPROPENE BY USING SAME

FIELD OF THE INVENTION

The present invention relates to a method for separating, from a mixture containing hydrogen chloride, 1-chloro-3,3,3-trifluoropropene and hydrogen fluoride, the 1-chloro-3,3,3-trifluoropropene and the hydrogen fluoride. The present invention also relates to a method for producing 1-chloro-3,3,3-trifluoropropene using such a separation method.

BACKGROUND ART 1-chloro-3,3,3-trifluoropropene (sometimes referred to as "1233"), which has a double bond in its structure and exhibits a very short lifetime in the air, is expected as being useful as an environment-adaptive hydrochlorofluorocarbon compound with no fear of ozone depletion and global warming. It is herein noted that, although 1-chloro-3,3,3-trifluoropropene can exist as trans and cis geometric isomers (sometimes referred to as "1233E" and "1233Z", respectively), the term "1-chloro-3,3,3-trifluoropropene" used in the present specification refers to a trans isomer solely or a trans/cis mixture that contains a trans isomer as a main component and further contains an cis isomer.

It is feasible to produce 1-chloro-3,3,3-trifluoropropene by fluorinating 1,1,1,3,3-pentachloropropane (sometimes referred to as "240fa") or 1,1,3,3-tetrachloro-2-propene (sometimes referred to as "1230za") with hydrogen fluoride in the presence of a fluorination catalyst in a gas phase or a liquid phase.

For example, Patent Document 1 discloses a method for producing 1-chloro-3,3,3-trifluoropropene by reacting 1,1,1,3,3-pentachloropropane with hydrogen fluoride in a gas phase. In the production method of Patent Document 1, the purity of the 1-chloro-3,3,3-trifluoropropene is improved by bringing the reaction product into contact with water and thereby removing the hydrogen fluoride from the reaction product. Patent Document 2 discloses a method for producing 1-chloro-3,3,3-trifluoropropene by reacting 1,1,1,3,3-pentachloropropane with hydrogen fluoride at a temperature of 180° C. or higher without the use of a solvent. Further, the liquid-phase production of 1-chloro-3,3,3-trifluoropropene is generally conducted under pressurized conditions so that the resulting 1-chloro-3,3,3-trifluoropropene is obtained as a compatible mixture containing unreacted hydrogen fluoride and by-produced hydrogen chloride (hereinafter sometimes referred to as "HCl") under pressure.

In the production process of a fluoroolefin, hydrogen fluoride is commonly used as a fluorination agent. As the fluoroolefin and the hydrogen fluoride are often compatible with each other, it is often the case that the product of the production process is in the form of a compatible mixture in which the fluoroolefin and the hydrogen fluoride are mutually dissolved.

In the case where the boiling point of the fluoroolefin is close to the boiling point (20° C.) of the hydrogen fluoride, the fluoroolefin and the hydrogen fluoride often form an azeotropic composition or azeotropic-like composition so that it becomes difficult to separate and purify the fluoroolefin and the hydrogen fluoride from the mixture thereof by distillation. It is herein noted that the term "azoptropic composition" refers to a mixture in which liquid and vapor phases in equilibrium are the same in composition; and the term "azeotropic-like composition" refers to a mixture in which liquid and vapor phases in equilibrium are similar in composition. These mixtures are difficult to separate by distillation.

It has been common practice to remove the hydrogen fluoride from the above-mentioned mixture by absorption of the hydrogen fluoride into water or an aqueous alkaline solution. In this technique, however, it is necessary to use a large amount of water for the removal of the hydrogen fluoride. It is also necessary to perform dehydration or drying operation for the removal of water content from the fluoroolefin. The dehydration or drying operation is complicated and requires equipment therefor. In general, the hydrogen fluoride can be removed by dilution with water and neutralization with an aqueous alkaline solution of sodium hydroxide, potassium hydroxide, calcium hydroxide, calcium carbonate etc. In industrial fields, the dilution of the hydrogen fluoride with the water and the neutralization of the hydrogen fluoride with the aqueous alkaline solution are often called "water washing" and "alkaline washing", respectively.

Patent Document 3 discloses a method for separating, from a composition containing a fluoroolefin and hydrogen fluoride, the fluoroolefin by extracting the composition with an extractant.

Patent Document 4 discloses a method for producing 1-chloro-3,3,3-trifluoropropene, including the steps of: reacting 1,1,1,3,3-pentachloropropane at a temperature lower than 150° C. in the presence of a Lewis acid catalyst or a mixture thereof in a liquid phase within a reactor; continuously extracting the resulting hydrogen chloride and 1-chloro-3,3,3-trifluoropropene from the reactor; and isolating the 1-chloro-3,3,3-trifluoropropene from the extracted product. In Examples of Patent Document 4, the purity of the 1-chloro-3,3,3-trifluoropropene is improved by removing the hydrogen fluoride from the mixture of the 1-chloro-3,3,3-trifluoropropene and the hydrogen fluoride with the use of potassium hydroxide.

In the case of producing 1-chloro-3,3,3-trifluoropropene by reaction of 1,1,1,3,3-pentachloropropane with hydrogen fluoride, the resulting product is in the form of a solution mixture in which the 1-chloro-3,3,3-trifluoropropene, unreacted hydrogen fluoride and by-produced hydrogen chloride are mutually dissolved. In order to obtain the 1-chloro-3,3,3-trifluoropropene as simple substance, it is necessary to separate the 1-chloro-3,3,3-trifluoropropene from the hydrogen fluoride. However, the 1-chloro-3,3,3-trifluoropropene (boiling point: 19° C.) is azeotropic with the hydrogen fluoride (boiling point: 20° C.). Even when the separation of the 1-chloro-3,3,3-trifluoropropene and the hydrogen fluoride is attempted by distillation, it is very difficult to separate the 1-chloro-3,3,3-trifluoropropene and the hydrogen fluoride due to azeotrope formation between the 1-chloro-3,3,3-trifluoropropene and the hydrogen fluoride. Although it is conceivable to remove the hydrogen fluoride by absorption into the water or an aqueous alkaline solution, such removal operation requires much expense in time and effort and equipment as mentioned above.

For example, Patent Document 5 discloses a method for separating 1-chloro-3,3,3-trifluoropropene and hydrogen fluoride by distillation.

The separation method of Patent Document 5 is intended to separate the hydrogen fluoride from the azeotropic mixture of the 1-chloro-3,3,3-trifluoropropene and the hydrogen fluoride where it is rich in hydrogen fluoride, i.e., where the hydrogen fluoride is higher in content than the 1-chloro-3,3,3-trifluoropropene. In this separation method, the pure hydrogen fluoride is obtained as a distillation bottom product (distillation residue) whereas the azeotropic mixture of the remaining hydrogen fluoride and the 1-chloro-3,3,3-trifluoropropene is obtained as a distillate. As mentioned above, however, it is generally difficult to separate the hydrogen fluoride and the 1-chloro-3,3,3-trifluoropropene by distillation due to azeotrope formation between the 1-chloro-3,3,3-trifluoropropene and the hydrogen fluoride. Although it is conceivable to remove the hydrogen fluoride by absorption into water or an aqueous alkaline solution, such removal operation has to use a large amount of water and requires much expense in time and effort and equipment to dispose of the resulting hydrogen fluoride water and dehydrate and dry the 1-chloro-3,3,3-trifluoropropene. Under the above circumstances, there has been a demand to develop a method for separating 1-chloro-3,3,3-trifluoropropene and hydrogen fluoride by simple operation without complicated operation and equipment.

In this way, when 1,1,1,3,3-pentachloropropane or 1,1,3,3-tetrachloro-2-propene is fluorinated with excessive hydrogen for the industrial production of 1-chloro-3,3,3-trifluoropropene, the 1-chloro-3,3,3-trifluoropropene is obtained as a compatible mixture containing unreacted hydrogen fluoride and by-produced hydrogen chloride. It is not easy to separate such a compatible mixture of 1-chloro-3,3,3-trifluoropropene, hydrogen fluoride and hydrogen chloride by distillation due to azeotrope formation between the 1-chloro-3,3,3-trifluoropropene and the hydrogen fluoride. Further, it requires much expense in time and effort and equipment to remove the hydrogen fluoride by absorption into water or an aqueous alkaline solution.

PRIOR ART DOCUMENTS

Patent Documents

Patent Document 1: Japanese Laid-Open Patent Publication No. H9-183740
Patent Document 2: Japanese Laid-Open Patent Publication No. H11-180908
Patent Document 3: Japanese Laid-Open Patent Publication (Japanese Translation of International Patent Publication) No. 2009-543783
Patent Document 4: Japanese Laid-Open Patent Publication (Japanese Translation of International Patent Publication) No. 2007-501843
Patent Document 5: Japanese Laid-Open Patent Publication No. H11-279088

SUMMARY OF THE INVENTION

Problems to be Solved by the Invention

As mentioned above, the production of the 1-chloro-3,3,3-trifluoropropene faces the problem that, from the mixture containing the produced 1-chloro-3,3,3-trifluoropropene, unreacted hydrogen fluoride and by-produced hydrogen chloride, the 1-chloro-3,3,3-trifluoropropene cannot be easily separated due to azeotrope formation between the 1-chloro-3,3,3-trifluoropropene and the hydrogen fluoride.

The present invention has been made to solve the above problem. It is an object of the present invention to provide an industrially useful, economical method for rapidly separating, from a mixture containing hydrogen chloride, 1-chloro-3,3,3-trifluoropropene and hydrogen fluoride, separating the n1-chloro-3,3,3-trifluoropropene and the hydrogen fluoride by simple operation.

Means for Solving the Problems

The present inventors have made extensive researches on the liquid-phase reaction of 1,1,1,3,3-pentachloropropane with hydrogen fluoride by varying the pressure and temperature of the reaction system after the reaction, and then, noticed that the resulting mixture of hydrogen chloride, 1-chloro-3,3,3-trifluoropropene and hydrogen fluoride could be separated into upper and lower phases. In this case, the hydrogen fluoride and the 1-chloro-3,3,3-trifluoropropene are contained in relatively large amounts in the upper and lower phases, respectively. However, the content of the hydrogen fluoride in the upper phase and the content of the 1-chloro-3,3,3-trifluoropropene in the lower phase are not so high. As a results of further extensive researches, the present inventors have found that it is possible to separate the mixture of the hydrogen chloride, 1-chloro-3,3,3-trifluoropropene and hydrogen fluoride into a hydrogen fluoride-rich upper phase predominantly containing the hydrogen fluoride and a 1-chloro-3,3,3-trifluoropropene-rich lower phase predominantly containing the 1-chloro-3,3,3-trifluoropropene within the reactor by reducing the content of the hydrogen chloride in the mixture. The present inventors have further found that it is possible to increase the content of the hydrogen fluoride in the upper phase and the content of the 1-chloro-3,3,3-trifluoropropene in the lower phase by controlling the temperature and pressure during the phase separation. Based on these findings, the present invention has been completed to provide a separation method of 1-chloro-3,3,3-trifluoropropene and hydrogen fluoride and a production method of 1-chloro-3,3,3-trifluoropropene using such a separation method. The separation method of the present invention is advantageous for industrial production applications because of the short time required for the phase separatio of the mixture.

Namely, the present invention includes the following inventive aspects 1-5.

[Inventive Aspect 1]

A separation method of 1-chloro-3,3,3-tetrafluoropropene and hydrogen fluoride, comprising: reducing the hydrogen chloride content of a mixture containing hydrogen chloride, 1-chloro-3,3,3-tetrafluoropropene and hydrogen chloride, thereby causing phase separation of the mixture so as to obtain an upper phase predominantly containing the hydrogen fluoride and a lower phase predominantly containing the 1-chloro-3,3,3-tetrafluoropropene.

[Inventive Aspect 2]

The separation method according to Inventive Aspect 1, wherein the phase separation is conducted at a temperature of −50° C. to 100° C.

[Inventive Aspect 3]

The separation method according to Inventive Aspect 1 or 2, wherein the phase separation is conducted at a pressure of 0.01 MPa to 2.1 MPa.

[Inventive Aspect 4]

A method for production of 1-chloro-3,3,3-trifluoropropene, comprising: bringing the lower phase obtained by the separation method according to any one of Inventive Aspects 1 to 3 into contact with water or an aqueous alkaline solution.

[Inventive Aspect 5]

The method for production of the 1-chloro-3,3,3-trifluoropropene according to Inventive Aspect 4, further comprising providing the mixture by fluorinating 1,1,1,3,3-pentachloropropane or 1,1,3,3-tetrachloro-2-propene with hydrogen fluoride such that the mixture contains the hydrogen fluoride as an unreacted reactant, the 1-chloro-3,3,3-tetrafluoropropene as a reaction product and the hydrogen chloride as a by-product.

In the separation method of the present invention, the phase separation between the 1-chloro-3,3,3-trifluoropropene and the hydrogen fluoride is caused by reducing the hydrogen chloride content of the mixture containing the hydrogen chloride, the 1-chloro-3,3,3-trifluoropropene and the hydrogen fluoride. The content of the hydrogen fluoride in the upper phase and the content of the 1-chloro-3,3,3-trifluoropropene are increased by controlling the temperature and pressure during the phase separation. Accordingly, the separation method of the present invention allows separation of the mixture into the hydrogen fluoride-rich upper phase and the 1-chloro-3,3,3-trifluoropropene-rich lower phase by simple operation without the need to use complicated equipment such as a washing device for absorption of the hydrogen fluoride into water or an aqueous alkaline solution or a distillation device. In addition, there are less load and short time required for the separation. The separation method of the present invention is thus advantageous for industrial production applications.

The production method of the 1-chloro-3,3,3-trifluoropropene, which includes the step of phase separation between the 1-chloro-3,3,3-trifluoropropene and hydrogen fluoride by the separation method of the present invention, is advantageous for industrial-plant production of the 1-chloro-3,3,3-trifluoropropene without the need for complicated operation and equipment.

DESCRIPTION OF THE EMBODIMENTS

Hereinafter, the present invention will be described in detail below.

It is known that a hydrocarbon having a plurality of fluorine atoms in its molecule exhibits high affinity for hydrogen fluoride and shows high solvability in hydrogen fluoride so that such a fluorohydrocarbon and hydrogen fluoride can easily form a compatible mixture. As 1-chloro-3,3,3-trifluoropropene is similarly compatible with hydrogen fluoride, it has been assumed that there would not occur phase separation between the 1-chloro-3,3,3-trifluoropropene and the hydrogen fluoride.

As a result of extensive researches, however, the present inventors have surprisingly found that hydrogen chloride serves as a compatibilizer between the 1-chloro-3,3,3-trifluoropropene and the hydrogen fluoride.

More specifically, the present inventors have made extensive researches on the liquid-phase reaction of 1,1,1,3,3-pentachloropropane or 1,1,3,3-tetrachloro-2-propene with hydrogen fluoride for the production of 1-chloro-3,3,3-trifluoropropene, and then, revealed that hydrogen chloride is generated as a by-product of the liquid-phase reaction and serves as a compatibilizer to increase compatibility between the produced 1-chloro-3,3,3-trifluoropropene and unreacted hydrogen fluoride and let the reaction solution remain as a compatible mixture without causing phase separation of the reaction solution. For example, the inside pressure of the reactor after the liquid-phase reaction is high due to the by-production of the hydrogen chloride. The compatible mixture is formed by dissolution of the hydrogen chloride in the reaction solution under such high-pressure conditions. The present inventors have found that, by removing only the hydrogen chloride from the reaction system and reducing the content, i.e., concentration of the hydrogen chloride in the reaction solution, it is possible to separate the reaction solution into an upper phase predominantly containing the hydrogen fluoride and a lower phase predominantly containing the 1-chloro-3,3,3-tetrafluoropropene. The present inventors have made further extensive researches on the conditions of such separation operation and found that, at the time of separating the reaction solution into the hydrogen fluoride-rich upper phase and the 1-chloro-3,3,3-trifluoropropene-rich lower phase, it is possible to increase the content of the hydrogen fluoride in the upper phase and the content of the 1-chloro-3,3,3-trifluoropropene in the lower phase and attain improvement in separability by controlling the pressure and temperature of the reaction system.

1. Separation of 1-chloro-3,3,3-trifluoropropene and Hydrogen Fluoride.

A separation method of 1-chloro-3,3,3-tetrafluoropropene and hydrogen fluoride according to the present invention includes reducing the hydrogen chloride content of a mixture containing hydrogen chloride, 1-chloro-3,3,3-tetrafluoropropene and hydrogen fluoride, thereby causing phase separation of the mixture so as to obtain a hydrogen fluoride-rich upper phase predominantly containing the hydrogen fluoride and a 1-chloro-3,3,3-tetrafluoropropene-rich lower phase predominantly containing the 1-chloro-3,3,3-tetrafluoropropene. In this separation method, the content of the hydrogen fluoride in the upper phase is at least 70 mol % or more based on the total amount of the hydrogen chloride, the 1-chloro-3,3,3-tetrafluoropropene and the hydrogen fluoride; and the content of the 1-chloro-3,3,3-tetrafluoropropene in the lower phase is at least 50 mol % or more based on the total amount of the hydrogen chloride, the 1-chloro-3,3,3-tetrafluoropropene and the hydrogen fluoride. The above mixture may contain a small amount of a raw material compound such as 1,1,1,3,3-pentachloropropane or 1,1,3,3-tetrachloro-2-propene, a catalyst and any other by-product component in addition to the hydrogen chloride, the 1-chloro-3,3,3-tetrafluoropropene and the hydrogen fluoride.

In general, the production of the 1-chloro-3,3,3-tetrafluoropropene is conducted by a gas-phase process in which 1,1,1,3,3-pentachloropropane or 1,1,3,3-tetrafluoro-2-propene is subjected to gas-phase fluorination with hydrogen fluoride by introduction into a fixed-bed gas-phase reactor packed with a solid Lewis acid catalyst such as fluorinated alumina or by a liquid-phase process in which 1,1,1,3,3-pentachloropropane or 1,1,3,3-tetrafluoro-2-propene is subjected to liquid-phase fluorination with hydrogen fluorination under pressurized condition in the presence of a Lewis acid catalyst or in the absence of a catalyst.

In either of the gas-phase process and the liquid-phase process, the resulting reaction product is in the form of a mixture containing organic substance, mainly 1-chloro-3,3,3-tetrafluoropropene as the target compound, unreacted hydrogen fluoride and by-produced hydrogen chloride when the fluorination is carried out by the use of an excessive amount of hydrogen fluoride. In this fluorination reaction, 4 mol of the hydrogen chloride is generated as the by-product when 1 mol of the 1-chloro-3,3,3-trifluoropropene is produced using 1 mol of the 1,1,1,3,3-pentachloropropane as the raw material.

In particular, the reaction product is obtained as a gas-liquid mixture under high pressure in the liquid-phase process. The hydrogen chloride is contained in the gas phase of the gas-liquid mixture, whereas the hydrogen chloride, the 1-chloro-3,3,3-trifluoropropene and the excessive hydrogen fluoride are contained and mixed in the liquid phase of the gas-liquid mixture. More specifically, the hydrogen chloride dissolved as the by-product in the liquid phase serves as a compatibilizer to cause mutual dissolution of the 1-chloro-3,3,3-trifluoropropene and the hydrogen fluoride so that the liquid phase becomes a mixture containing the hydrogen chloride, the 1-chloro-3,3,3-trifluoropropene and the hydrogen fluoride.

In the separation method of the present invention, the hydrogen chloride content of the mixture can be reduced by e.g. cooling and condensing/liquefying the mixture and then purging the hydrogen chloride (boiling point: −85° C.) from the mixture, or controlling the temperature of the mixture. Industrially, only the hydrogen chloride can be removed from the reaction system through a condenser or reflux column. The compatible mixture of the hydrogen fluoride and the 1-chloro-3,3,3-trifluoropropene is then separated into the hydrogen fluoride-rich upper phase and the 1-chloro-3,3,3-trifluoropropene-rich lower phase. By such hydrogen chloride reduction process, the hydrogen chloride content of the mixture is preferably controlled to 20 mol % or less based on the total amount of the mixture. Namely, the hydrogen chloride content of the mixture before the phase separation is preferably 20 mol % or more in the separation method of the present invention. In industrial production applications, it is generally often the case that the hydrogen chloride content of the mixture before the phase separation is 30 mol % or more.

In the separation method of the present invention, the phase separation is preferably conducted at a temperature of −50° C. to 100° C. If the phase separation temperature is lower than −50° C., it is difficult to conduct the phase separation by means of an ordinary refrigerator. Such low-temperature phase separation is excessively high in equipment cost and is impractical for use in industrial plants. There is no need to conduct the phase separation at a temperature higher than 100° C. The phase separation temperature is more preferably in the range of −20° C. to 80° C.

Further, the phase separation is preferably conducted at a pressure of 0.01 MPa to 2.1 MPa in the separation method of the present invention. If the phase separation pressure is lower than 0.01 MPa, it is difficult to separate the hydrogen fluoride and the 1-chloro-3,3,3-trifluoropropene unless under low-temperature conditions so that the phase separation is impractical for industrial production applications. If the phase separation pressure is higher than 2.1 MPa, it is difficult to separate the hydrogen fluoride and the 1-chloro-3,3,3-trifuoropropene due to compatibility between the hydrogen fluoride and the 1-chloro-3,3,3-trifuoropropene. The phase separation pressure is more preferably in the range of 0.1 MPa to 1.1 MPa. It is herein noted that the pressure is in units of absolute pressure (Pa).

In the separation method of the present invention, the phase separation is preferably conducted under the conditions (temperature and pressure) where the hydrogen fluoride does not become vaporized.

After the phase separation, the hydrogen fluoride can be easily recovered from the hydrogen fluoride-rich upper phase by e.g. removing the hydrogen chloride with the use of a reflux column as compared to the case without the phase separation. On the other hand, the 1-chloro-3,3,3-trifluoropropene can be efficiently recovered from the separated 1-chloro-3,3,3-trifluoropropene-rich lower layer by e.g. removing the hydrogen fluoride and the hydrogen chloride by contact and absorption into water or an aqueous alkaline solution. At this time, there is no need to use a large amount of the water or aqueous alkaline solution. The 1-chloro-3,3,3-trifluoropropene may further be subjected to precision distillation. In either case, the above recovery process is significantly simplified in operation as compared to the case without the phase separation.

In the case of using the 1-chloro-3,3,3-trifluoropropene as a raw material for the production of 1,1,1,3,3-pentafluoropropane, there is no need to preform contact absorption treatment with water or an aqueous alkaline solution. The 1-chloro-3,3,3-trifluoropropene-rich lower phase can be used as it is as the raw material.

2. Production of 1-chloro-3,3,3-trifluoropropene

A production method of 1-chloro-3,3,3-trifluoropropene according to the present invention includes bringing the lower phase obtained by the above separation method into contact with water or an aqueous alkaline solution.

In this production method, the mixture to be subjected to phase separation is preferably provided by fluorinating 1,1,1,3,3-pentachloropropane or 1,1,3,3-tetrachloro-2-propene with hydrogen fluoride such that the mixture contains the hydrogen fluoride as an unreacted reactant, the 1-chloro-3,3,3-tetrafluoropropene as a reaction product and the hydrogen chloride as a by-product.

Hereinafter, the processes for the production of the 1-chloro-3,3,3-trifluoropropene will be explained successively.

2-1. Process for Providing Mixture

It is feasible to provide the mixture containing the hydrogen fluoride, the 1-chloro-3,3,3-trifluoropropene and the hydrogen fluoride by any known technique. As mentioned above, the 1-chloro-3,3,3-trifluoropropene can be produced by fluorinating 1,1,1,3,3-pentachloropropane or 1,1,3,3-tetrachloro-2-propane with hydrogen fluoride in the presence of a fluorination catalyst in a gas phase or in a liquid phase within a reactor.

For example, when the 1,1,1,3,3-pentachloropropane and excessive hydrogen fluoride are heated at 150° C. in the absence of a catalyst within the reactor, there occurs replacement reaction to replace chlorine atoms of trichloromethyl group of the 1,1,1,3,3-pentachloropropane with fluorine atoms and thereby form the 1-chloro-3,3,3-tetrafluoropropene as the target compound and the hydrogen chloride as the by-product. The resulting reaction product is thus obtained as the mixture containing the hydrogen chloride, the 1-chloro-3,3,3-tetrafloropropene and the hydrogen fluoride. In this reaction, the inside pressure of the reactor reaches 4 to 5 MPa. Further, this reaction may be performed with the addition of a catalyst such as $SbCl_5$.

2-2. Process for Reducing Hydrogen Chloride in Mixture

By reducing the hydrogen chloride content of the mixture, the mixture is separated into the hydrogen fluoride-rich upper phase and the 1-chloro-3,3,3-trifluoropropene-rich lower phase in the subsequent phase separation process.

In the case where the mixture containing the hydrogen fluoride, the 1-chloro-3,3,3-trifluoropropene and the hydrogen fluoride is being pressurized in the reactor after the liquid-phase reaction, for example, it is feasible to selectively remove the hydrogen chloride from the gas phase and thereby reduce the hydrogen chloride content of the mixture by releasing the pressure from the reactor.

At this time, the pressure of the reactor is generally in proportion to the hydrogen chloride content of the mixture. The pressure can be thus used an index of the concentration of the hydrogen chloride in the solution. The pressure is preferably in the range of 0.01 MPa to 2.1 MPa, more preferably 0.1 MPa to 1.1. MPa.

It is preferable that the lower the content of the hydrogen chloride that serves as a compatibilizer between the 1-chloro-3,3,3-trifluoropropene and the hydrogen fluoride, the clearer the boundary between the upper and lower phases during the phase separation for the lower concentration of the hydrogen fluoride in the 1-chloro-3,3,3-trifluoropropene-rich lower phase and the lower concentration of the 1-chloro-3,3,3-trifluoropropene in the hydrogen fluoride-rich upper phase.

2-3. Process for Conducting Phase Separation

By reducing the hydrogen chloride content of the mixture containing the hydrogen chloride, the 1-chloro-3,3,3-trifluoropropene and the hydrogen fluoride, the mixture is spontaneously separated into the hydrogen fluoride-rich upper phase and the 1-chloro-3,3,3-trifluoropropene-rich lower phase. During the separation, it is preferable to cool the mixture obtained by the above mixture providing process. The cooling temperature is generally −50° C. to 100° C. It becomes easier by the cooling to separate the mixture into the hydrogen fluoride-rich upper phase and the 1-chloro-3,3,3-trifluoropropene-rich lower phase.

2-4. Process for Bringing Lower Phase into Contact with Water or Aqueous Alkaline Solution In the production method of the present invention, the separated 1-chloro-3,3,3-trifluoropropene-rich lower phase is subjected to absorption treatment with the water or aqueous alkaline solution and then with zeolite in order to improve the purity of the 1-chloro-3,3,3-trifluoropropene. By such treatment process, the 1-chloro-3,3,3-trifluoropropene is obtained containing substantially no hydrogen fluoride and hydrogen chloride.

Even if the residual 1-chloro-3,3,3-trifluoropropene is contained in the hydrogen fluoride-rich upper phase, there is no need to obtain the hydrogen fluoride with high purity by separation and purification treatment of the hydrogen fluoride-rich upper phase in the case where the hydrogen fluoride is recycled as the raw material for the above fluorination of the 1,1,1,3,3-pentachloropropane.

EXAMPLES

The separation method of the hydrogen fluoride and the 1-chloro-3,3,3-trifluoropropene according to the present invention will be described in more detail below by way of the following examples. It is however noted that the following examples are illustrative only and are not intended to limit the present invention thereto.

Example 1

Separation of Hydrogen Fluoride and 1-chloro-3,3,3-trifluoropropene

In a 2000-ml stainless steel autoclave, 433 g (2 mol) of 1,1,1,3,3-pentachloropropane and 300 g (15 mol) of hydrogen fluoride were placed. The autoclave was kept heated at 200° C. under a pressure of about 10 MPa for 5 hours. After the reaction, the resulting hydrogen chloride was purged out of the reactor while the autoclave was cooled in a dry ice/acetone bath. As a result, 332 g of a fraction having a boiling point of about 20° C. was obtained. This fraction had two separate phases. When the acid content of the lower organic phase was measured by titration, the content of hydrogen fluoride in the lower organic phase was found to be 2.4 mass % (14 mol %). When the lower organic phase was washed with water and then analyzed by gas chromatography, trans-1-chloro-3,3,3-trifluoropropene (1233zd) was found as a component of the lower organic phase. There was found no other component in the lower organic phase.

It has been confirmed by the results of Example 1 that it is possible to easily recover the 1-chloro-3,3,3-trifluoropropene by the separation method of the present invention, i.e., by reducing the hydrogen chloride content of the mixture containing the hydrogen chloride, 1-chloro-3,3,3-trifluoropropene and hydrogen fluoride.

Example 2

Influence of Pressure

Provided was a 500-ml stainless steel autoclave with an agitator. After the inside of the autoclave was vacuumed, the autoclave was cooled at 0° C. in an ice water bath. Subsequently, 265 g of 1-chloro-3,3,3-trifluoropropene and 125 g of hydrogen fluoride nwere introduced into the autoclave. By this, a mixture of 1-chloro-3,3,3-trifluoropropene:hydrogen fluoride=1:3 (mol ratio) was prepared. While the mixture was stirred by an agitation blade within the autoclave, hydrogen chloride was gradually added in gaseous form into the autoclave. Then, the mixture in which the 1-chloro-3,3,3-trifluoropropene, the hydrogen fluoride and the hydrogen chloride were mutually dissolved was obtained. The temperature of the autoclave was increased to 30° C while the mixture was stirred by the agitation blade. By the temperature increase, the hydrogen chloride was vaporized from the mixture so that the pressure of the autoclave was raised to 0.3 MPa or 0.6 MPa. Herein, the amount of the hydrogen chloride added was adjusted so as to control the pressure of the autoclave to 0.3 MPa or 0.6 MPa by the temperature increase to 30° C. Due to the vaporization of the hydrogen chloride, the concentration of the hydrogen chloride in the mixture was decreased. After stopping the stirring, the mixture was left still for 10 minutes. When composition analysis was performed on upper and lower sides of the content of the mixture, there was found two separate phases: an upper phase predominantly containing the hydrogen fluoride and a lower phase predominantly containing the 1-chloro-3,3,3-trifluoropropene. For the sake of convenience, the upper phase predominantly containing the hydrogen fluoride and the lower phase predominantly containing the 1-chloro-3,3,3-trifluoropropene are hereinafter referred to as "hydrogen fluoride phase (HF phase)" and "1-chloro-3,3,3-trifluoropropene phase (1233zd phase)", respectively.

The compositions of the hydrogen fluoride phase and the 1-chloro-3,3,3-trifluoropropene phase are indicated in TABLE 1.

TABLE 1

| Pressure (MPa) | HF phase | | | 1233zd phase | | |
|---|---|---|---|---|---|---|
| | HCl mol % | HF mol % | 1233zd mol % | HCl mol % | HF mol % | 1233zd mol % |
| 0.3 | 15.3 | 79.1 | 5.6 | 5.2 | 17.0 | 77.8 |
| 0.6 | 3.5 | 85.2 | 11.3 | 10.4 | 25.3 | 64.3 |

As is seen from TABLE 1, the content of the hydrogen fluoride in the hydrogen fluoride phase and the content of the 1-chloro-3,3,3-trifluoropropene in the 1-chloro-3,3,3-trifluoropropene phase were 79.1 mol % and 77.8 mol %, respectively, when the pressure was 0.3 MPa. When the pressure was 0.6 MPa, the content of the hydrogen fluoride in the hydrogen fluoride phase and the content of the 1-chloro-3,3,3-trifluoropropene in the 1-chloro-3,3,3-trifluoropropene phase were 85.2 mol % and 64.3 mol %, respectively. It has been confirmed by these results that the separation method of 1-chloro-3,3,3-trifluoropropene and hydrogen fluoride according to the present invention is effective.

Example 3

Influence of Temperature

A mixture of hydrogen chloride, 1-chloro-3,3,3-trifluoropropene and hydrogen fluoride was prepared and treated in an autoclave in the same manner as in Example 2, except for adjusting the amount of the hydrogen chloride added so as to control the pressure of the autoclave to 0.6 MPa at 1.9° C., 18.7° C., 29.1° C. or 45.6° C. After the treatment, the content of the autoclave was separated into a hydrogen fluoride phase and a 1-chloro-3,3,3-trifluoropropene phase under the conditions of temperature of 1.9° C., 18.7° C., 29.1° C. or 45.6° C. and pressure of 0.6 MPa.

The compositions of the hydrogen fluoride phase and the 1-chloro-3,3,3-trifluoropropene phase are indicated in TABLE 2.

TABLE 2

| Temperature (° C.) | HF phase | | | 1233zd phase | | |
| --- | --- | --- | --- | --- | --- | --- |
|  | HCl mol % | HF mol % | 1233zd mol % | HCl mol % | HF mol % | 1233zd mol % |
| 1.9 | 4.8 | 88.3 | 6.9 | 17.1 | 17.3 | 65.6 |
| 18.7 | 3.5 | 88.5 | 8.0 | 12.2 | 25.5 | 62.3 |
| 29.1 | 3.5 | 87.5 | 9.0 | 10.5 | 27.3 | 62.2 |
| 45.6 | 1.9 | 88.1 | 10.3 | 3.5 | 38.5 | 58.0 |

As is seen from TABLE 2, the content of the hydrogen fluoride in the hydrogen fluoride phase and the content of the 1-chloro-3,3,3-trifluoropropene in the 1-chloro-3,3,3-trifluoropropene phase were 88.3 mol % and 65.6 mol %, respectively, when the temperature was 1.9° C. When the temperature was 18.7° C., the content of the hydrogen fluoride in the hydrogen fluoride phase and the content of the 1-chloro-3,3, 3-trifluoropropene in the 1-chloro-3,3,3-trifluoropropene phase were 88.5 mol % and 62.3 mol %, respectively. When the temperature was 29.1° C., the content of the hydrogen fluoride in the hydrogen fluoride phase and the content of the 1-chloro-3,3,3-trifluoropropene in the 1-chloro-3,3,3-trifluoropropene phase were 87.5 mol % and 62.2 mol %, respectively. The content of the hydrogen fluoride in the hydrogen fluoride phase and the content of the 1-chloro-3,3,3-trifluoropropene in the 1-chloro-3,3,3-trifluoropropene phase were 88.1 mol % and 58.0 mol %, respectively, when the temperature was 45.6° C. In this way, both of the hydrogen fluoride content and the 1-chloro-3,3,3-trifluoropropene content were high at any temperature of 1.9° C., 18.7° C., 29.1° C. and 45.6° C. It has thus also been confirmed by these results that the separation method of 1-chloro-3,3,3-trifluoropropene and hydrogen fluoride according to the present invention is effective.

Example 4

Time for Phase Separation Between Hydrogen Fluoride and 1-chloro-3,3,3-trifluoropropene A mixture of hydrogen chloride, 1-chloro-3,3,3-trifluoropropene and hydrogen fluoride was prepared and treated in the same manner as in Examples 1 and 2, except for using a transparent cylindrical container of perfluoroalkoxy fluorocarbon resin (PFA) so as to visually check the time lapsed until the separation of the mixture into a hydrogen fluoride phase and a 1-chloro-3,3,3-trifluoropropene phase.

More specifically, the cylindrical PFA container used herein was 9.5 mm in inside diameter and 350 mm in length. After the inside of the container was vacuumed, the container was cooled in an ice water bath. The mixture was prepared by introducing the 1-chloro-3,3,3-trifluoropropene and the hydrogen fluoride at a ratio of 1-chloro-3,3,3-trifluoropropene:hydrogen fluoride=1:3 (mol ratio) as in Examples 1 and 2. The hydrogen chloride was gradually added in a predetermined amount into the container. While the temperature of the container was maintained at 0° C. or increased to 15° C., the mixture was stirred by an agitation blade. By this, the pressure of the container was raised to a predetermined level of 0.3 MPa or 0.6 MPa. The content of the container was vigorously stirred and suspended by shaking the container. When the container was left still, the phase boundary was visually observed. Then, the time lapsed until the separation into the hydrogen fluoride phase and the 1-chloro-3,3,3-trifluoropropene phase was measured.

The separation time measurement results are indicated in TABLE 3

TABLE 3

| Pressure (MPa) | Temperature (° C.) | Separation time (s) | | | |
| --- | --- | --- | --- | --- | --- |
|  |  | First measurement | Second measurement | Third measurement | Average |
| 0.6 | 0 | 42 | 42 | 40 | 41.3 |
| 0.6 | 15 | 41 | 30 | 40 | 40.0 |
| 0.3 | 0 | 26 | 24 | 23 | 24.3 |
| 0.3 | 15 | 22 | 22 | 23 | 22.3 |

The phase separation time was 39 to 42 seconds at 0.6 MPa and 22 to 26 seconds at 0.3 MPa. It is apparently advantageous in that, in industrial production applications, the time required for the phase separation process is short when the mixture of the 1-chloro-3,3,3-trifluoropropene and the hydrogen fluoride is separated into the 1-chloro-3,3,3-trifluoropropene-rich phase and the hydrogen fluoride-rich phase in a short time.

The invention claimed is:

1. A separation method of 1-chloro-3,3,3-trifluoropropene and hydrogen fluoride, comprising:
   reducing the hydrogen chloride content of a mixture containing hydrogen chloride, 1-chloro-3,3,3-trifluoropropene and hydrogen fluoride, thereby causing phase separation of the mixture so as to obtain an upper phase predominantly containing the hydrogen fluoride and a lower phase predominantly containing the 1-chloro-3,3, 3-trifluoropropene.

2. The separation method according to claim 1, wherein the phase separation is conducted at a temperature of −50° C. to 100° C.

3. The separation method according to claim 1, wherein the phase separation is conducted at a pressure of 0.01 MPa to 2.1 MPa.

4. A method for production of 1-chloro-3,3,3-trifluoropropene, comprising:
   fluorinating 1,1,1,3,3-pentachlorpropane or 1,1,3,3-tetrachloro-2-propene with hydrogen fluoride, therby providing a mixture containing hydrogen fluoride as an unreacted reactant, 1-chloro-3,3,3-trifluoropropene as a reaction product and hydrogen chloride as a by-product;
   reducing the hydrogen chloride content of the mixture, thereby causing phase separation of the mixture so as to obtain an upper phase predominantly containing the hydrogen fluoride and a lower phase predominantly containing the 1-chloro-3,3,3-trifluorpropene; and
   purifying the 1-chloro-3,3,3-trifluorpropene by bringing the lower phase into contact with water or an aqueous alkaline solution.

* * * * *